United States Patent [19]

Lembke et al.

[11] Patent Number: 4,834,987

[45] Date of Patent: May 30, 1989

[54] METHOD OF PREPARING FOOD AND COMPOSITION FOR PROTECTING MICROORGANISMS USED IN THE PREPARATION OF FOOD

[75] Inventors: Andreas Lembke, Eutin-Sielbeck; Rolf Deininger, Furst-Puckler; Jürgen Lembke, Eutin-Sielbeck, all of Fed. Rep. of Germany

[73] Assignee: Chimicasa GmbH, Fed. Rep. of Germany

[21] Appl. No.: 921,104

[22] Filed: Oct. 21, 1986

[30] Foreign Application Priority Data

Oct. 21, 1985 [LU] Luxembourg .................... 86129

[51] Int. Cl.$^4$ ................................. A23C 9/12
[52] U.S. Cl. ........................................ 426/9; 426/34; 426/43; 426/61; 435/260; 435/800
[58] Field of Search .............. 426/268, 9, 34, 43, 426/11, 36, 321, 334, 335, 7, 61, 72; 435/235, 236, 238, 253, 255, 256, 260, 800, 136

[56] References Cited

U.S. PATENT DOCUMENTS 4,310,553  1/1982  Odentsova ........................ 426/72
4,409,245  10/1983  Wolf et al. ........................ 426/9

OTHER PUBLICATIONS

Pike 1975 Nutrition: An Integrated Approach, 2nd edition John Wiley & Sons, Inc. New York pp. 115–122.
Chemical Abstracts 104: 10420s.

*Primary Examiner*—Donald E. Czaja
*Assistant Examiner*—Carolyn Paden
*Attorney, Agent, or Firm*—Saidman, Sterne, Kessler & Goldstein

[57] ABSTRACT

In the preparation of food with the aid of microorganisms, the latter are directly protected against viral or phage attack by the addition of formic acid or esters of formic acid or salts of formic acid and/or tetrahydrofolic acid. Furthermore, an indirect protection by inactivating the bacterial viruses in the environment is described.

15 Claims, No Drawings

METHOD OF PREPARING FOOD AND COMPOSITION FOR PROTECTING MICROORGANISMS USED IN THE PREPARATION OF FOOD

BACKGROUND OF THE INVENTION

1. Field of the Invention

The present invention relates to a method of protecting microorganisms against viral or phage attack and more specifically to a method of preparing food produced by means of a starter culture of microorganisms which is activated when needed and is protected against viral or phage attack. The starter culture is cultured to form an operating culture or is added directly into the substrate. The starter culture is converted in such a manner that the microorganisms are protected against phage attack by the addition of an anti-viral composition in a dose that is not detrimental to the fermentation by the added bacteria or to the enjoyment of the food. The invention further relates to a composition for carrying out the method.

2. Brief Description of the Background Art

The industrial preparation of food such as, for example, attenuation, cheese-making and fermentation, is performed with the aid of microorganisms, namely bacteria, yeasts, fungi or algae. These microorganisms are subject to attack by phages, which can disrupt the conversion processes for which the microorganisms are used. It is therefore desirable to counteract the phage attack.

EU-B1-3318 teaches a method of the type initially described in the Field of the Invention, in which black pepper oil is added as an anti-viral composition. In some instances, however, black pepper oil is not a desirable additive. It is therefore the object of the invention to modify a method of the type initially described above in such a manner that it can be carried out with an additive composition which is as harmless as possible and which causes no problems in the treated food.

It is a further object of the invention to teach a method of preparing an operating culture that is protected from phage attack.

SUMMARY OF THE INVENTION

The invention is characterized in that the anti-viral composition comprises at least ten percent of formic acid and/or esters of formic acid, preferably ethyl formate, and/or salts of formic acid, and/or tetrahydrofolic acid and/or that the remainder of the anti-viral composition consists of at least one of the following substances: Black pepper oil, cassia oil, cardamon oil, linoleyl acetate, cinnamic aldehyde, cinnamic acid ethyl ester, safrole, carvone and cis/trans citral.

DESCRIPTION OF THE PREFERRED EMBODIMENT

It is known that formic acid has a toxic action on microorganisms. However, the anti-viral action of formic acid, esters of formic acid, salts of formic acid, ethyl formate and tetrahydrofolic acid, as taught by the invention, is not known. Formic acid, as well as other possible additional substances cited as ingredients for the anti-viral composition, exhibits an anti-viral action, that is, an action adverse to phages, even at a concentration which is several orders of magnitude lower than the concentration at which formic acid, esters of formic acid, ethyl formate, salts of formic acid or tetrahydrofolic acid cause the known toxic action on microorganisms. This wide gap offers a tolerance margin which is advantageous during dosing and within which the desired anti-viral action can be achieved without simultaneously endangering the microorganisms to be protected from phages with the formic acid, esters of formic acid, ethyl formate, salts of formic acid and/or tetrahydrofolic acid.

Formic acid and tetrahydrofolic acid are essentially non-toxic for the human organism in the doses used and are therefore unobjectionable as food additives. Because the desired anti-viral action can be achieved with relatively small added amounts of formic acid, ethyl formate and tetrahydrofolic acid, the added formic acid, ethyl formate, and tetrahydrofolic acid will not adversely affect the taste the food. That is also conditionally true for the other possible components of the anti-viral composition.

Preferably, formic acid and/or esters of formic acid, preferably ethyl formate, and/or salts of formic acid, and/or tetrahydrofolic acid is/are added as the sole active ingredient, that is, as 100% of the anti-viral composition.

It is sufficient for the desired purpose and harmless for the microorganisms involved if 25 to 500 mg of the anti-viral active ingredient or combination of ingredients are added per 1 kg starter culture. The active ingredient(s) is (are) previously diluted in water or alcohol to 1–10%.

In order to protect the microorganisms, the anti-viral composition can be added to the starter culture and/or to the operating culture and/or to the food together with the operating culture. In general, however, it can be assumed that the starter cultures are sterile if they were produced industrially and will also be stored in a sterile manner. This sterility can be ensured by the addition of the anti-viral composition to the starter culture. If the starter culture was produced in the food industry, it is generally recommended that the starter culture also be protected with the anti-viral composition. The production of the operating culture, which is generally performed in the industry, is particularly problematic because sterile conditions are so hard to maintain. For this reason, the anti-viral composition is preferably added during preparation or in conjunction with the operating culture.

If the operating culture is prepared in a closed tank, it is often impossible to prevent ambient air infected with phages from entering the tank. A further development of the invention takes this circumstance into account and is characterized in that an operating culture is produced in a tank which is provided with pressure compensation means, is otherwise closed and which comprises closable openings and is sterilized by pressurized steam, in that heated milk is introduced into the heated, sterilized tank, in which any phages still present have been thermally inactivated, in that during the cooling-off phase the anti-viral composition is sprayed into the tank with an atomizer utilizing the pressure difference between the outer area and the inner area of the tank, in that after the cooling, the active starter culture is introduced into the tank with an appropriate device, is thoroughly mixed and cultured there to produce the operating culture, and in that the starter culture treated with the anti-viral composition is aseptically introduced into the tank with an appropriate device.

pumpkins, carrots, beans, other vinegar products and the like, using microorganisms suitable for this purpose.

The examples can also be varied with regard to the anti-viral composition used. The anti-viral composition used can be comprised of not only formic acid but also of esters of formic acid or, especially, of ethyl formate, salts of formic acid and/or tetrahydrofolic acid or of mixtures of formic acid and esters of formic acid. Moreover, along with formic acid or esters of formic acid, the anti-viral composition can also contain one or more of the initially cited active ingredients with an admixture ratio such as initially stated.

What is claimed is:

1. A method of preparing food in which a starter culture of microoganisms is produced and maintained in a storable state, in which the starter culture is reactivated when needed and cultured to produce an operating culture, in which the operating culture is inoculated into the food to be prepared and living conditions which are conducive to the desired action by the inoculated microorganisms are maintained in the food during the inoculation and thereafter for the duration of the desired action, and in which the microorganisms are protected against viral or phage attack, said method comprising the addition of an antiviral composition in an amount effective to protect said microorganisms from viral or phage attack but ineffective to harm said microorganisms or said food and its enjoyment, wherein said antiviral composition comprises from 10% to 100% by weight of an antiviral compound selected from the group consisting of formic acid, esters of formic acid, salts of formic acid, tetrahydrofolic acid, or mixtures thereof as the active ingredient, and wherein any remainder of said anti-viral composition comprises at least one of the following substances: black pepper oil, cassia oil, cardamon oil, linoleyl acetate, cinnamic aldehyde, cinnamic acid ethyl ester, safrole, carvone, and cis/trans citral.

2. The method of claim 1, wherein said anti-viral composition consists essentially of formic acid, esters of formic acid, preferably ethyl formate, salts of formic acid, tetrahydrofolic acid, or mixtures thereof.

3. The method of any one of claims 1 or 2, wherein 25 to 500 mg (milligrams) of said anti-viral composition active ingredient is used per 1 kg (kilogram) of said starter- culture and said active ingredient(s) is (are) diluted in advance to 1–10% in alcohol or water.

4. The method of any one of claims 1, 2 or 3, wherein said anti-viral composition is added to said starter culture.

5. The method of any one of claims 1 to 5, wherein said anti-viral composition is not added until the production of the operating culture.

6. The method of claim 5, wherein said operating culture is produced by a method comprising sterilizing and heating a pressure tank with pressurized steam; adding heated milk to said heated and sterilized tank, whereby any phages still present in said milk are thermally inactivated; cooling said tank and said milk; spraying the inside of said tank with an anti-viral composition during said cooling; aseptically introducing into said tank said starter culture; and mixing and culturing said starter culture with said milk.

7. The method of any one of claims 1–6, wherein said method is applied, in the preparation of products using bacteria as said microorganism in said starting culture.

8. The method of any one of claims 1–6, wherein said method is applied in the preparation of products using yeast as said microorganism in said starting culture.

9. An anti-viral starter culture composition for protecting microorganisms used in food preparation from viral or phage attack, comprising a suspension of microorganisms and an anti-viral component comprising at least a 10% by weight portion of a compound selected from the group consisting of formic acid, salts of esters of formic acid, tetrahydrofolic acid, or a mixture thereof, as the active ingredient 10. The anti-viral starter culture composition of claim 9, wherein the remaining portion of said anti-viral component further comprises one or more members selected from the group consisting of black pepper oil, cassia oil, cardamon oil, linoleyl acetate, cinnamic aldehyde, cinnamic acid ethyl ester, safrole, carvone and cis/transcitral.

11. An anti-viral composition for protecting microorganisms used in the preparation of food against viral of phage attack in accordance claim 9, wherein said composition comprises a compound selected from the group consisting of formic acid, esters of formic acid, salts of formic acid, tetrahydrofolic acid, or mixtures thereof, mixed into a solvent in a mixture ratio of 1:10 to 1:1000, wherein said solvent can be easily mixed into the food and is suitable as a harmless food additive.

12. An anti-viral composition for protecting microorganisms used in the preparation of food against viral of phage attack in accordance claim 9, wherein a mixture of formic acid is mixed into a solvent in a mixture ratio of 1:10 to 1:1000, wherein solvent can be easily mixed into said food and is suitable as a harmless food additive, and said mixture is selected from a group consisting of formic acid, esters of formic acid, salts of formic acid, tetrahydrofolic acid or mixtures thereof as an active ingredient in an amount from 10% to 100% by weight, and wherein any remainder of said composition comprises at least one of the following substances, which can be extracted from aromatic plants, in a weight mixture ratio of 9:1 to 1:9 : black pepper oil, cassia oil, cardamon oil, linoleyl acetate, cinnamic aldehyde, cinnamic acid ethyl ester, safrole, carvone and cis/trans citral.

13. The composition of any of claims 9, 10, 11 or 12 wherein said solvent is ethanol or water.

14. The composition of any of claims 9, 10, 11 or 12 wherein said microorganisms are bacteria.

15. The composition of any of claims 9, 10, 11 or 12 wherein said microorganisms are yeast.

* * * * *

UNITED STATES PATENT AND TRADEMARK OFFICE
CERTIFICATE OF CORRECTION

PATENT NO. : 4,834,987

DATED : May 30, 1989

INVENTOR(S) : Lembke et al.

It is certified that error appears in the above-identified patent and that said Letters Patent is hereby corrected as shown below:

The sheet consisting of columns 3 and 4 should be inserted as per attached sheet. (Grant Only)

Signed and Sealed this

Twenty-third Day of January, 1990

*Attest:*

JEFFREY M. SAMUELS

*Attesting Officer*     *Acting Commissioner of Patents and Trademarks*

The gaseous filling of the cooling-down container is mixed with the vaporized, anti-viral composition and thereby becomes anti-viral. Additional gas or air which is generally not sterile and penetrates into the tank for pressure compensation during cooling is sterilized in this manner as regards its phage content.

The invention also relates to a composition for protecting microorganisms used to prepare food against attack by phages. Such a composition comprises formic acid and/or esters of formic acid, preferably ethyl formate, and/or salts of formic acid, and/or tetrahydrofolic acid mixed into a carrier substance in a mixture ratio of 1:10 to 1:1000, whereby the carrier substance can be easily mixed into the food and is suitable as a harmless food additive.

Instead of using pure formic acid, it is also possible to use the other substances mentioned above, which can be extracted from aromatic plants, in such a composition. An appropriate composition is characterized in that a formic acid mixture is mixed into a carrier substance, in a mixture ratio of 1:10 to 1:1000, whereby the carrier substance is easy to mix into the food and is suitable as a harmless food additive, and is further characterized in that this formic acid mixture comprises formic acid and/or esters of formic acid, preferably ethyl formate, and/or salts of formic acid, and/or tetrahydrofolic acid, into which one or more of the following substances, which can be extracted from aromatic plants, are mixed in a weight-based mixture ratio of 9:1 to 1:9 : Black pepper oil, cassia oil, cardamon oil, linoleyl acetate, cinnamic aldehyde, cinnamic acid ethyl ester, safrole, carvone and cis/trans citral.

Tests have shown that a harmless dose of the anti-viral composition suitable for use with most of the useful microorganisms can be 1:1000 and for some even 1:100. On the other hand, an admixture ratio of 1:2000 to 1:100,000, corresponding to the protecting mass, is sufficient as an anti-viral does. That results in a margin of several orders of magnitude within which the dose can readily fall with a safe anti-viral action without endangering the microorganisms.

On account of the great range, a large, dose of the anti-viral composition, which is harmless to the microorganisms and humans, can be added to the starter culture. This admixture is then diluted in the operating culture and on account of the great marginal range, it is easy to set the ratios in such a manner that the reduced admixture ratio of the anti-viral composition in the operating culture which results from the dilution is still sufficient for the desired anti-viral action, so that no additional anti-viral composition need be added to the operating culture.

The invention can be used, among other applications, in the preparation of milk to fermented milk, yogurt or cheese with the aid of *Streptococcus lactis, Streptococcus cremoris, Streptococcus diacetylactis, Leuconostoc cremoris, Streptococcus thermophilus* or *Lactobacillus bulgaricus*; in the attenuation of beer wort with the aid of a *Saccharomyces cerevisiae* and for the preparation of sauerkraut, cucumbers, pumpkins, carrots, beans, other vinegar products and the like using the appropriate microorganisms.

The invention will now be explained in more detail in several examples.

DESCRIPTION OF THE PREFERRED EMBODIMENTS

EXAMPLE 1

In order to produce yogurt, a starter culture of *Streptococcus thermophilus* and *Lactobacillus bulgaricus* is prepared. A maximum of 500 mg formic acid per 1 kg starter culture in the form of a ten percent solution is mixed into the starter culture as an anti-viral composition. Then, the starter culture is stored in deep-frozen portions. When needed, a portion of the starter culture is thawed out and mixed under sterile conditions into presterilized, warm milk. The operating culture is produced from this mixture. The operating culture, divided into portions, is then added in the required concentrations to warmed milk and yogurt is formed after incubation.

The anti-viral composition is contained in the starter culture in a dose which does not damage the microorganisms. In the operating culture, the anti-viral composition is diluted only to the extent that a sufficient anti-viral action still remains.

EXAMPLE 2

Same as Example 1, with the sole difference that the anti-viral composition is not added to the starter culture until the starter culture is used to produce the operating culture.

EXAMPLE 3

In order to produce yogurt, a starter culture of *Streptococcus thermophilus* and *Lactobacillus bulgaricus* is prepared. Then, the starter culture is stored in deep-frozen portions.

A 1,300 L (liters), tank, which is provided with closable openings, but is otherwise closed, is sterilized with pressurized steam. Then, 1,000 L of heated milk, in which any possible phages have been thermally inactivated, are filled into the tank. During the filling phase, the overlying air space (e.g. 200 L) is saturated with the anti-viral composition, in the form of an aerosol. The anti-viral composition, e.g., 2 L of a 0.2% solution, is sprayed into the tank by an atomizer, utilizing the pressure difference between the outer and the inner tank areas. The starter culture or the starter culture treated with the anti-viral composition is aseptically introduced into the tank with a suitable device. The liquid in the tank is mixed and allowed to stand approximately 4 hours at 40° C. The milk is converted in this manner into the final product - yogurt.

EXAMPLE 4

Formic acid is dissolved in water in a weight ratio of 1:50. The solution is sterilized in an autoclave. The composition obtained in this manner is added to the food to be prepared by microorganisms in a weight ratio of 2.5 g to 25 g of the composition to 1 kg food, which corresponds to 50 to 500 mg formic acid to 1 kg food.

The examples given above can be used with other microorganisms, for example, *Streptococcus cremoris, Streptococcus diacetylactis, Leuconostoc cremoris, Streptococcus thermophilus* or *Lactobacillus bulgaricus*. They can be used with other foods, for example, in the attenuation of beer wort with the aid of a *Saccharomyces cerevisiae* and for the preparation of sauerkraut, cucumbers,